(12) United States Patent
Heijnen et al.

(10) Patent No.: US 6,566,119 B1
(45) Date of Patent: May 20, 2003

(54) METHOD FOR ACQUIRING GRAIN-SHAPED GROWTH OF A MICROORGANISM IN A REACTOR

(75) Inventors: Joseph Johannes Heijnen, NR-Rijen (NL); Marinus Cornelis Maria Van Loosdrecht, HL de Lier (NL)

(73) Assignee: Technische Universiteit Delft, Delft (NL)

( * ) Notice: Subject to any disclaimer, the term of this patent is extended or adjusted under 35 U.S.C. 154(b) by 0 days.

(21) Appl. No.: 09/367,985

(22) PCT Filed: Feb. 19, 1998

(86) PCT No.: PCT/NL98/00100

§ 371 (c)(1),
(2), (4) Date: Oct. 14, 1999

(87) PCT Pub. No.: WO98/37027

PCT Pub. Date: Aug. 27, 1998

(30) Foreign Application Priority Data

Feb. 21, 1997 (NL) .............................. 1005345

(51) Int. Cl.[7] .............................. C12N 1/00; C12N 1/02
(52) U.S. Cl. ...................... 435/243; 435/261; 435/822; 435/911
(58) Field of Search ................ 435/243, 261, 435/822, 911

(56) References Cited

U.S. PATENT DOCUMENTS 3,864,246 A * 2/1975 Casey et al. .................. 210/7
4,623,464 A * 11/1986 Ying et al. .................. 210/616
4,891,136 A * 1/1990 Voyt .......................... 210/605

FOREIGN PATENT DOCUMENTS

| DE | 9301791 | | 5/1995 |
| EP | 0 776 864 A1 | | 6/1997 |
| JP | 7-68293 | * | 3/1995 |
| WO | WO 93/15025 | | 8/1993 |

OTHER PUBLICATIONS

Lettinga et al. Antonie van leeuwenhoek. 1995. 67:3–28.*
Shin et al. Wat. Sci. Tech. 1992. vol. 26, No. 3–4, pp. 601–605.*
Benefield et al. Water Air Siol Pollution. 1975. vol. 5, No. 1, pp. 113–123.*
Dague et al. J. Water Pollut. Control. Fed. 1966. vol. 38, No. 2, pp. 220–226.*
Abstract, Mitsubishi Kakoki Kaisha Ltd. Application No. 04169908, Jun. 5, 1992.

* cited by examiner

Primary Examiner—Sandra E. Saucier
Assistant Examiner—Vera Afremova
(74) Attorney, Agent, or Firm—Darby & Darby

(57) ABSTRACT

The invention relates to a method of acquiring granular growth of a microorganism in a reactor containing a liquid medium. Surprisingly, according to the invention, aerobic microorganisms also can be induced to granular growth by maintaining specific culture conditions. During a first step an oxygen-containing gas is supplied and the reactor contents are kept in turbulence. In a second step, after a short settling period, the top part of the reactor medium is discharged.

7 Claims, 2 Drawing Sheets

METHOD FOR ACQUIRING GRAIN-SHAPED GROWTH OF A MICROORGANISM IN A REACTOR

FIELD OF THE INVENTION

The present invention relates to a method of acquiring granular growth of a microorganism in a reactor containing a liquid phase which comprises a substrate, wherein in a first step said substrate is converted by the microorganism resulting in the formation of and growth on a phase comprising the organism while the liquid phase is being mixed, in a second step mixing in the reactor is stopped to allow part of the solid phase to settle, and in a third step the reactor is partly emptied by discharging the top part of the reactor contents, which reactor is subsequently replenished with substrate-comprising liquid, to repeat steps 1 to 3.

BACKGROUND OF THE INVENTION

Such a method has been described by Sung S. et al. (Laboratory studies of the anaerobic sequencing batch reactor, in Water Environment Research, 67 (3), p. 294, 1995). In this method an anaerobic conversion is carried out, the contents of the reactor are then clarified in characteristically 10–30 minutes after which the top part of the reactor contents is discharged. According to this publication work with anaerobically activated sludge has long been known, although it was not recognized in the beginning (1966) that what was occurring was "granulation" of the biomass. Granulation under methanogenic conditions (that is to say in the absence of oxygen) is often explained by the specific need of the respective organisms to exchange substrates the so-called "interspecies hydrogen transfer", or to reduce the toxicity of oxygen.

SUMMARY OF THE INVENTION

Surprisingly, applicant has found that granulation can also occur under aerobic and turbulent conditions.

The method according to the invention is therefore characterized in that the microorganism is an aerobic microorganism, in that at least during the first step a third phase is present, which third phase comprises oxygen-containing gas being fed to the reactor during the first step while the contents of the reactor are kept in turbulence, and in that settling occurs in the second step and takes less time than the height of liquid in the reactor at the end of the first step divided by a settling velocity of at least 5 meters per hour.

The formation of granules under turbulent aerobic conditions is unexpected, because organisms in a granule are under very great stress as due to the size of the granule, nutrients have to diffuse over large distances before reaching the interior of a granule. The fact that in addition aerobic organisms require oxygen, increases the stress still more so that one would expect such aerobic organisms only to flocculate. In addition, the expert would expect the granules to disintegrate due to the great shearing forces caused by the turbulence.

In the present application an aerobic microorganism is understood to be both an obligate and a facultative aerobic microorganism.

Preferably the compound is fed to the reactor in pulses. This causes the organisms in a granule to be flooded with compound. As the organisms at the outside of the granule are unable to process such a supply of compound, the compound gets the opportunity to diffuse into the interior of the granule. This is especially important if the compound to be converted is a nutrient. An example of this is carbohydrate fermentation for the preparation of lactic acid.

In accordance with a favourable embodiment the contents of the reactor are substantially continuously mixed during the first step.

To promote the formation of aggregates, Sung et al. prefer periodical mixing during which only slight shearing forces occur. According to the invention, however, continuous turbulent mixing subjects flocs to mixing forces, allowing them to be discharged more easily in the third step. In addition, applicant has established by experimentation that if microorganisms are subjected to great shearing forces, the result is a more robust granule. Thus according to the invention the organisms in the reactor form into granules more quickly.

Turbulent mixing is conveniently carried out by feeding oxygen-containing gas into, for instance, an airlift-reactor or bubbling-bed reactor.

An interesting application of the method according to the invention is characterized in that the conversion is a nitrification-denitrification-conversion in which the oxygen-containing gas is only supplied during the first part of the first step for the completion of the nitrification, and that the reactor operates during the remainder of the first step under substantially anaerobic conditions for the completion of the denitrification. If desired, the gas may during this first step be recirculated over the reactor. Due to recirculation all oxygen is used up and turbulence is maintained.

When applying the method according to the invention, the organism-comprising granules must be present, or at least conditions promoting the formation of granules must be provided before starting up the reactor. It is useful, for instance, to feed the reactor with carrier particles to which organisms adhere, or are able to adhere. It has been shown that a mycelium-forming fungus can also be used as carrier.

According to a very favourable embodiment settling occurs in the second step, taking less time than the height of liquid in the reactor at the end of the first step divided by a settling velocity of at least 10 meters per hour, preferably at least 15 meters per hour. Thus the presence of granules in the reactor is strongly favoured in comparison with the presence of flocs. As mentioned above, Sung et al. describe a clarification step taking characteristically 10 to 30 minutes. The settling velocity is then only 1 meter per hour, and applied to aerobic organisms such a method will not result in granulation. While under anaerobic conditions the clarification step merely serves to separate organisms and treated water, is also the clarification step in the method according to the invention of essential importance for the induction of granulation.

BRIEF DESCRIPTION OF THE DRAWINGS

The invention will now be explained with reference to an exemplary embodiment and with reference to the drawing, in which.

EXAMPLE 1

Figure 1:
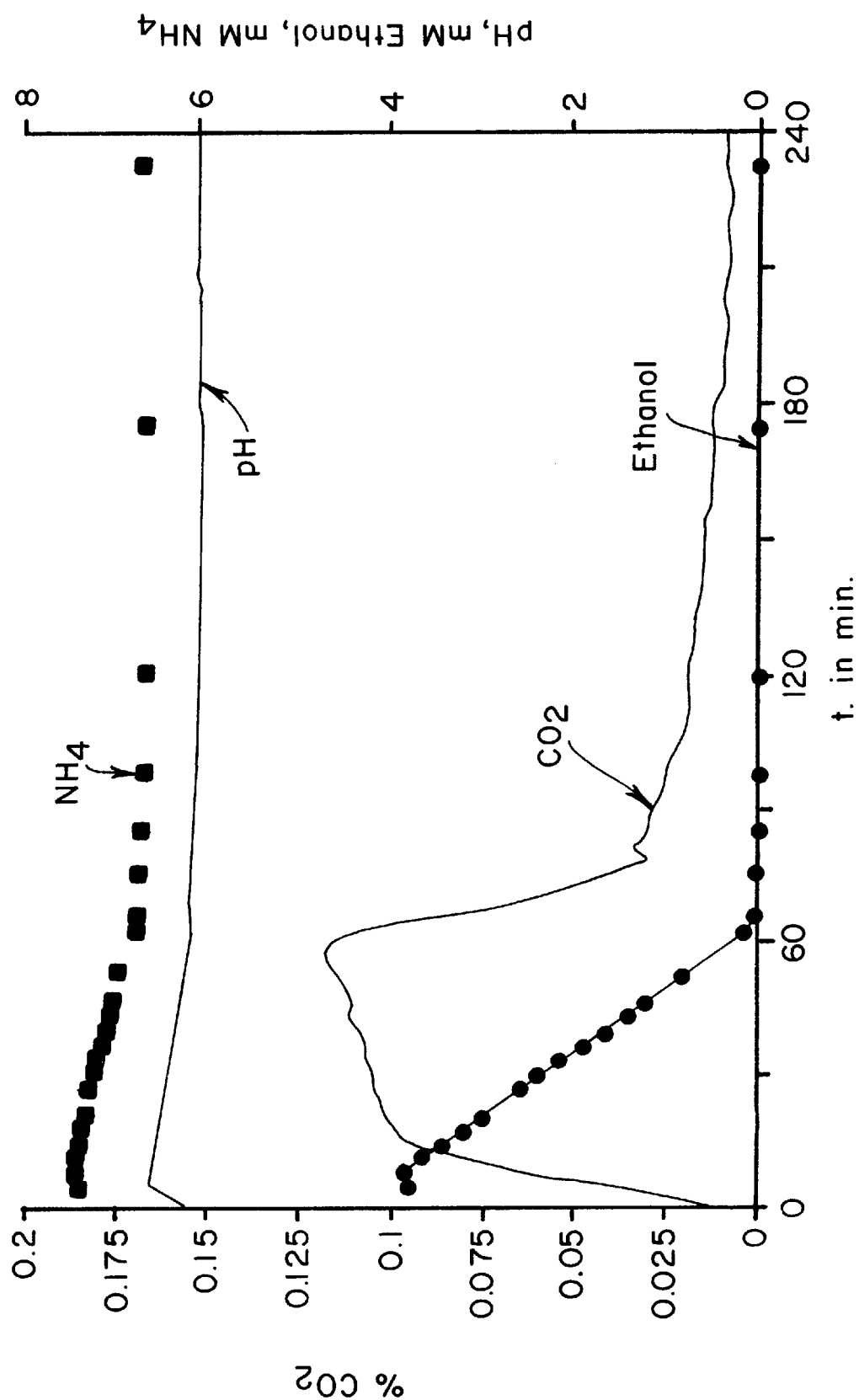
FIG. 1 is a graphical representation of the carbon dioxide percentage in gas discharged from a bubbling-bed reactor during a cycle of the method according to the invention.

A bubbling-bed reactor (2.5 liters; height/diameter 20) was fed with 1.25 liters of a solution serving as model for waste water, comprising 8.7 mM ethanol, 5 mM ammonium chloride, 4.7 mM potassium phosphate, 2.4 mM magnesium sulphate, 0.48 calcium chloride and per liter solution 1.5 ml of a standard solution of trace elements. The solution was inoculated with aerobically active sludge from a water treatment plant. The model waste water in the bubbling bed reactor was subjected to a cyclic treatment at pH 6–8 and a temperature of 20° C. The treatment consisted of i) aerating for 4 hours at a flow rate of 1.5 liters air per minute (FIG. 1 shows the carbon dioxide percentage in the gas discharged from a bubbling-bed reactor during this phase. This percentage is a measure of the conversion of the ethanol), ii) the one-minute stoppage of aeration, and iii) draining model waste water from the bubbling-bed reactor at the half-way point of the column of liquid. Any biomass present during draining in the top half of the solution, was discharged together with the effluent. Finally, iv) the bubbling-bed reactor was replenished with a volume of model waste water equal to that of the discharged effluent. The cycle was then resumed with four hours aeration of the solution.

Figure 2:
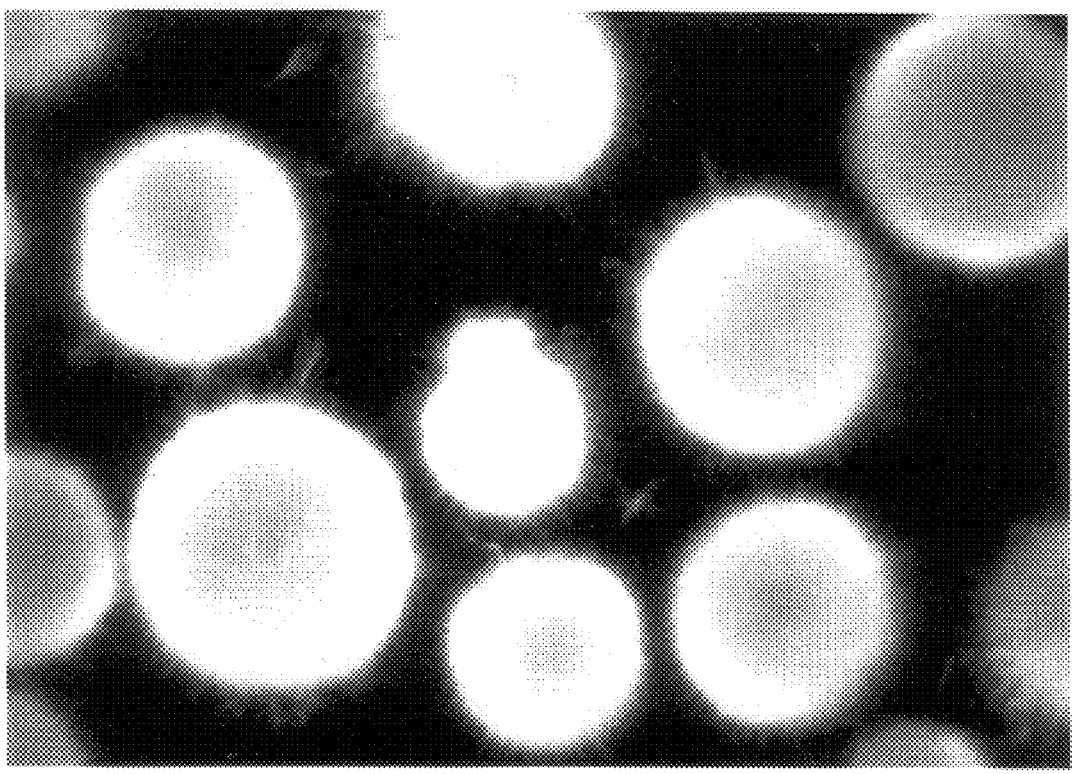
FIG. 2 is an illustration of a granule composed of aerobic organisms.

FIG. 2 shows the granules comprised of aerobic microorganisms, obtained by the method according to the invention. The average size is 3 mm.

What is claimed is:

1. A method of acquiring granular growth of an aerobic microorganism in a reactor comprising a liquid and a substrate, the method comprising the steps of:

(a) inoculating a reactor with an aerobic microorganism;

(b) feeding the reactor with a liquid comprising a substrate;

(c) feeding a gas comprising oxygen to the reactor, to cause turbulent mixing of the liquid, substrate and aerobic microorganism, wherein the substrate is converted by the aerobic microorganism to form a plurality of aerobic microorganism granules;

(d) stopping the mixing for a period of time, so that the aerobic microorganism granules settle in the reactor;

(e) draining the reactor by partly emptying the top part of the reactor;

wherein the aerobic microorganism granules settle during step (d) for a period of time which is determined by calculating a value that is the height of the liquid in the reactor at the end of step (c) in meters divided by a settling velocity of at least 5 meters per hour; and repeating steps (b) to (e).

2. The method of claim 1 wherein in step (b) the liquid comprising a substrate is fed in pulses.

3. The method of claim 1, wherein the conversion of the substrate in step (c) is a nitrification-denitrification-conversion in which the gas comprising oxygen is only supplied during the first part of step (c) for the completion of the nitrification, and the reactor operates during the remainder of the step under substantially anaerobic conditions for the completion of the denitrification.

4. The method of claim 1, wherein step (a) further comprises inoculating the reactor with a carrier particle for the microorganism.

5. The method of claim 4, wherein the carrier particle comprises a mycelium-forming fungus.

6. The method of claim 1, wherein the settling velocity is at least 10 meters per hour.

7. The method of claim 1, wherein the settling velocity is at least 15 meters per hour.

* * * * *